United States Patent
Lemoine et al.

(10) Patent No.: US 10,702,594 B2
(45) Date of Patent: Jul. 7, 2020

(54) DRIED SAPONIN LIPOSOMAL COMPOSITION

(71) Applicant: GLAXOSMITHKLINE BIOLOGICALS SA, Rixensart (BE)

(72) Inventors: Dominique Ingrid Lemoine, Rixensart (BE); Nicolas Moniotte, Maryland, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/061,137

(22) PCT Filed: Dec. 13, 2016

(86) PCT No.: PCT/EP2016/080814
§ 371 (c)(1),
(2) Date: Jun. 11, 2018

(87) PCT Pub. No.: WO2017/102737
PCT Pub. Date: Jun. 22, 2017

(65) Prior Publication Data
US 2018/0360939 A1      Dec. 20, 2018

(30) Foreign Application Priority Data
Dec. 15, 2015    (GB) .................................. 1522068.4

(51) Int. Cl.
*A61K 39/00* (2006.01)
*A61K 39/12* (2006.01)
(Continued)

(52) U.S. Cl.
CPC ........ *A61K 39/0015* (2013.01); *A61K 9/1275* (2013.01); *A61K 9/19* (2013.01); *A61K 39/00* (2013.01); *A61K 39/015* (2013.01); *A61K 39/12* (2013.01); *A61K 39/29* (2013.01); *A61K 2039/545* (2013.01);
(Continued)

(58) Field of Classification Search
CPC .... A61K 39/0015; A61K 9/19; A61K 9/1275; A61K 39/00; A61K 39/12; A61K 39/015
See application file for complete search history.

(56) References Cited

FOREIGN PATENT DOCUMENTS

WO    2007068907 A2    6/2007
WO    2007071707 A2    6/2007
(Continued)

OTHER PUBLICATIONS

Hua et al, "Freeze-Drying of Liposomes with Cryoprotectants and Its Effect on Retention Rate of Encapsulated Ftorofur and Vitamin A", Dry Technology, vol. 21, Issue 8, pp. 1491-5005. (Year: 2007).*

*Primary Examiner* — Carlos A Azpuru
(74) *Attorney, Agent, or Firm* — Birch, Stewart, Kolasch & Birch, LLP.

(57) ABSTRACT

Described herein is the formulation of immunogenic or vaccine compositions comprising neutral lipid liposome based adjuvants, where the composition is suitable for lyophilisation. In particular, the invention relates to lyophilised forms of such immunogenic or vaccine compositions wherein both the immunogen or vaccine antigen and the adjuvant are present in one and the same vial, as well as to the formulation and manufacture of lyophilised forms of such immunogenic or vaccine composition.

22 Claims, 8 Drawing Sheets

(51) Int. Cl.
*A61K 39/015* (2006.01)
*A61K 9/127* (2006.01)
*A61K 9/19* (2006.01)
*A61K 39/29* (2006.01)

(52) U.S. Cl.
CPC ............. *A61K 2039/55555* (2013.01); *A61K 2039/55572* (2013.01); *A61K 2039/55577* (2013.01); *A61K 2039/6075* (2013.01); *C07K 2319/00* (2013.01); *C12N 2710/16734* (2013.01); *Y02A 50/412* (2018.01)

(56) References Cited

FOREIGN PATENT DOCUMENTS

| | | | |
|---|---|---|---|
| WO | 2010/142686 A1 | * | 12/2010 |
| WO | 2012080369 A1 | | 6/2012 |
| WO | 2012160199 A1 | | 11/2012 |
| WO | 2013041572 A1 | | 3/2013 |

* cited by examiner

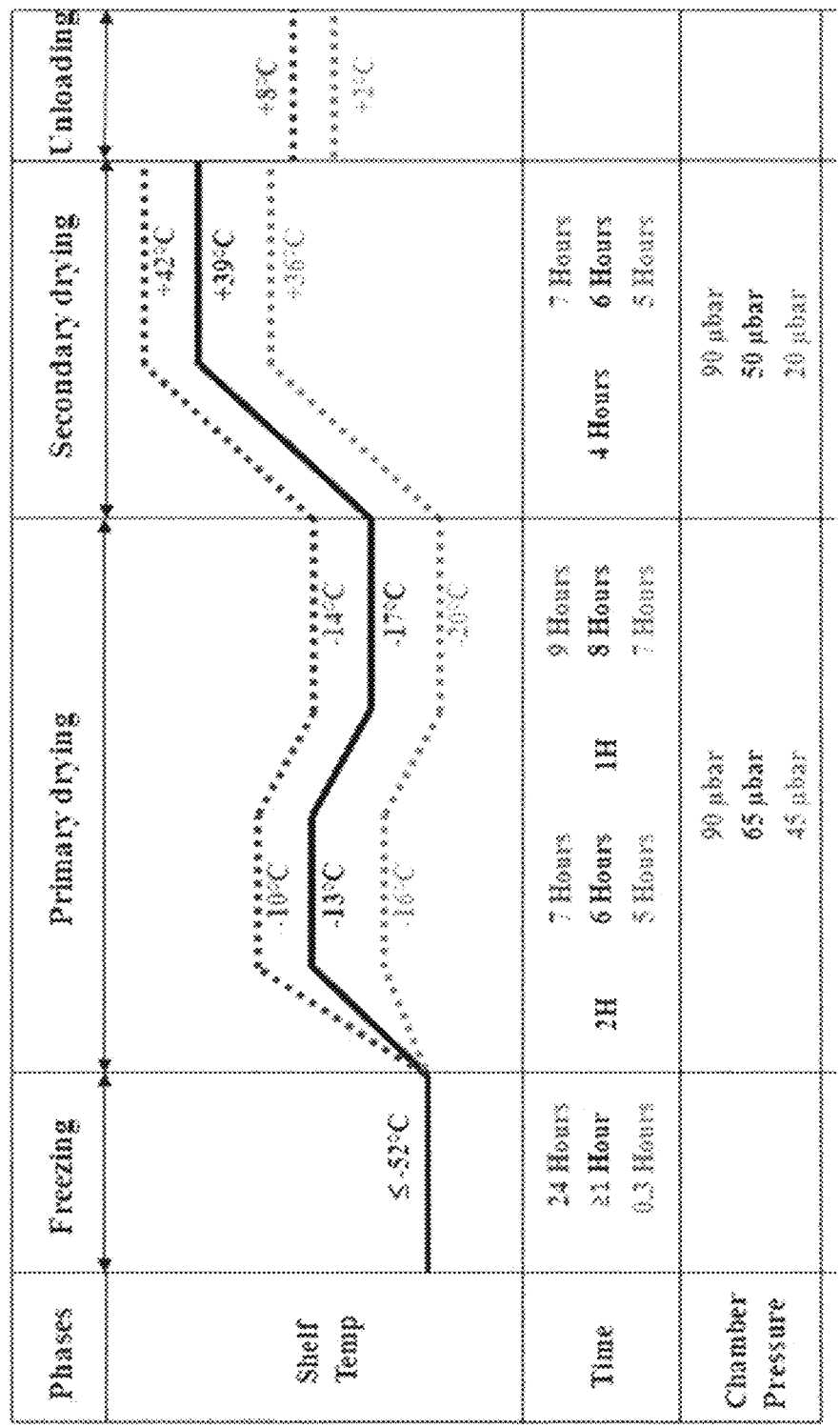
Figure 1-A

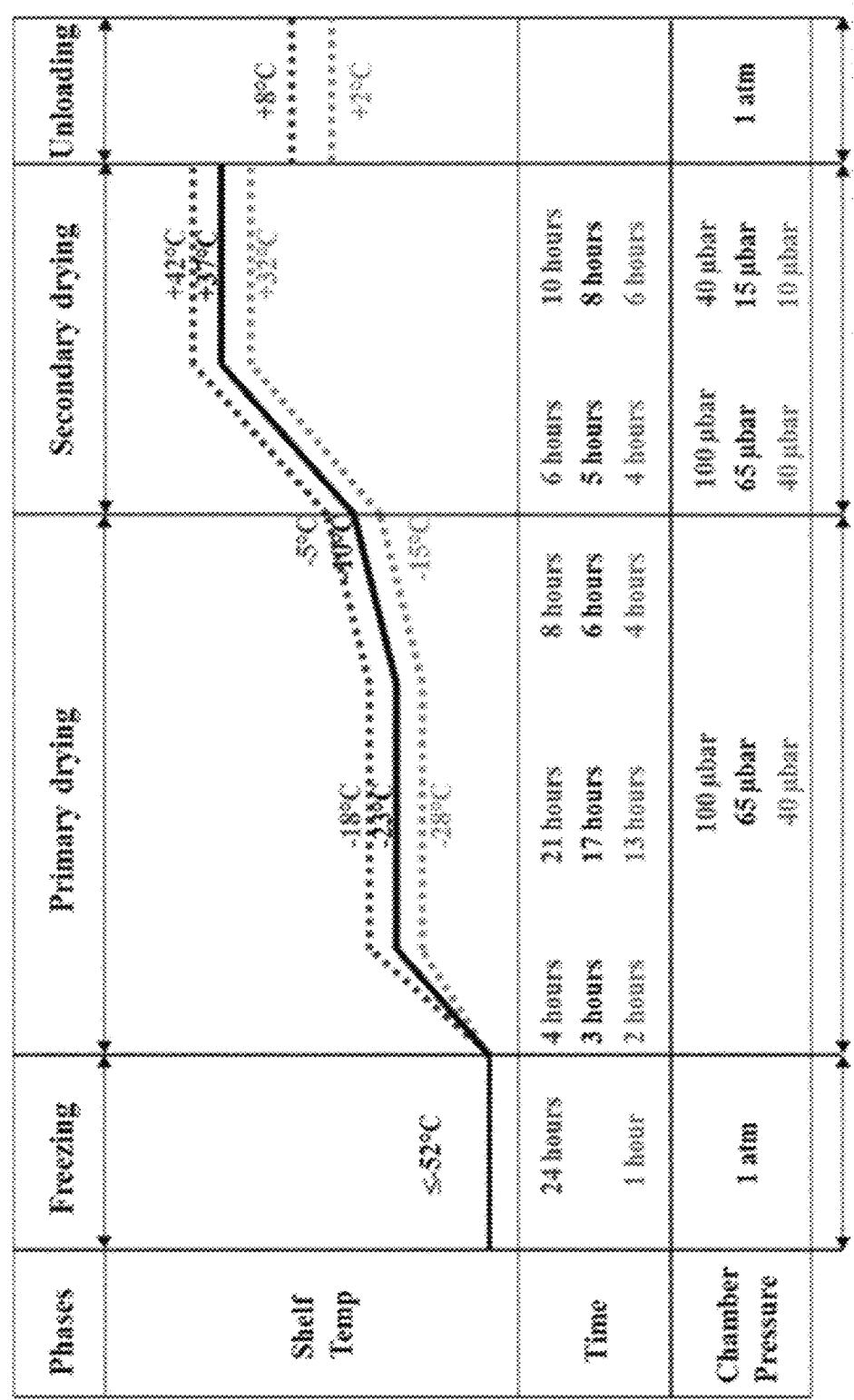
Figure 1-B

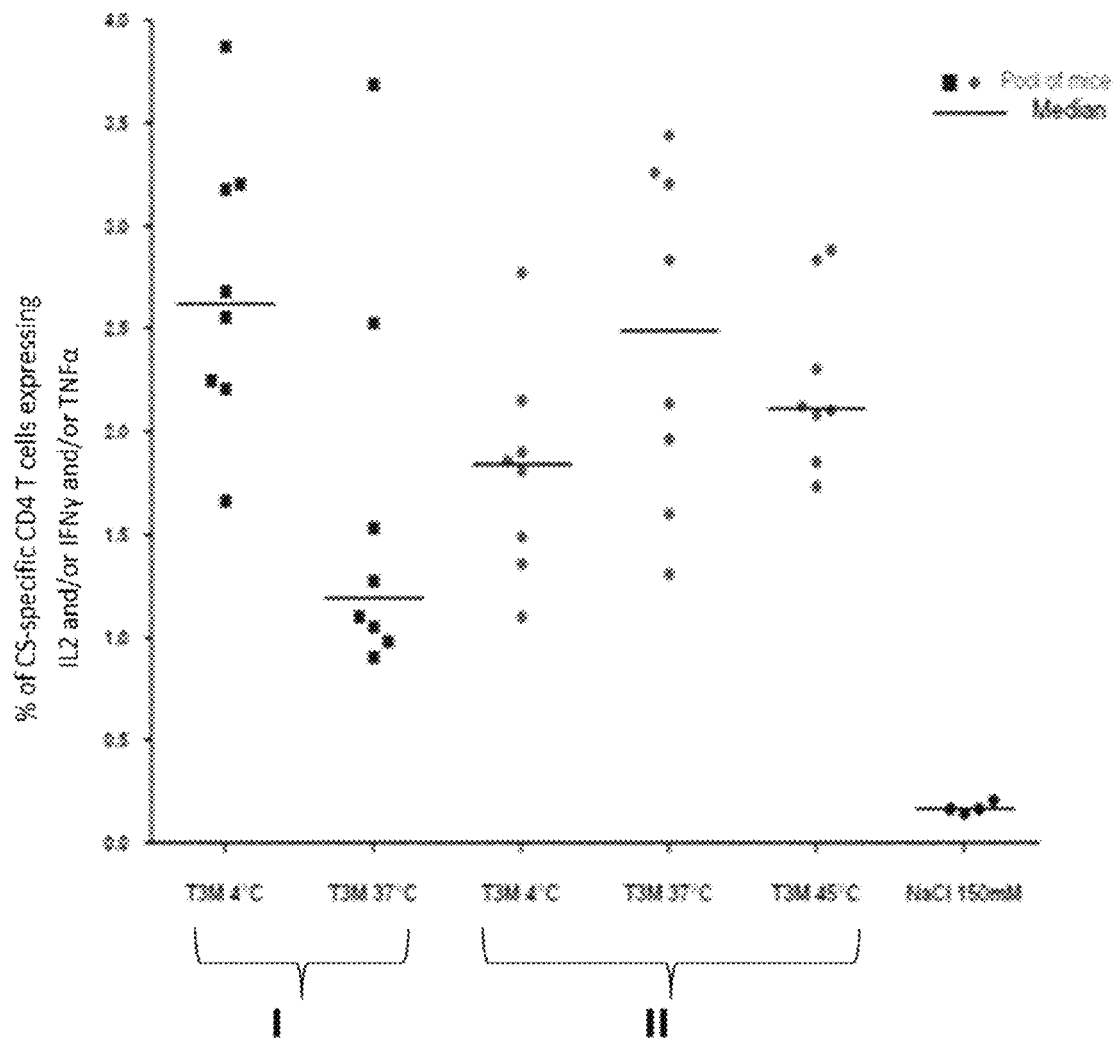
Figure 2-A

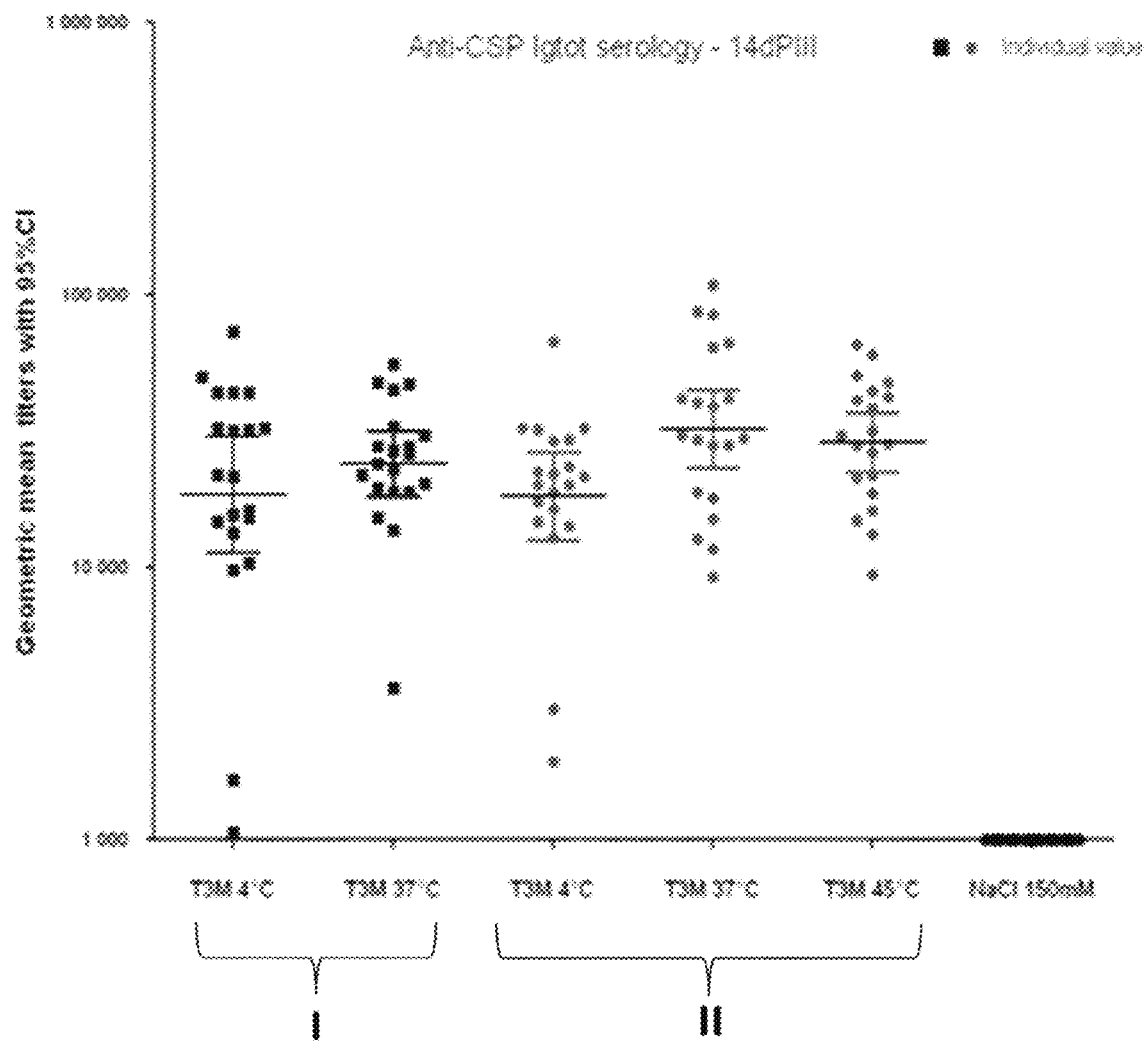
Figure 2-B

```
  1 MGTVNKPVVG VLMGFGIITG TLRITNFVRA SVLRYDDFHI DEDKLDTNSV YEPYYHSDHA
 61 ESSWVNKGES SRKAYDHNSP YIWFRNDYDG FLENAHEHHG VYNQGPGIDS GERLMQPTQM
121 SAQEDLGDDT GIHVIFTLNG DDRHKIVTVD QRQYGDVFKG DLNPKPQGQR LIEVSVEENK
181 PFTLRAFIQR IYGVRYTETW SFLFSITCTG DAAFAIQHIC LKHTTCFQDV VVDVDCAENT
241 KEDQLAEISY RFQKKEADQ PWIVVNTSTL FUELELDPPE IEPGVLKVLK TEKQYLGVYI
301 WUMRGSDGTS TYATFLVTWK GDEKTRMPTP AVTPQPPGAE FHMWNYKSHV FSVGDTFSLA
361 MHLQYKIHEA PFDLLLEWLY VPIDFTCQPM RLYSTCLYHP NAPQCLSHMN SGCTFTSPHL
421 AQFVASTVYQ SCEHADNYTA YCLJISHMSP SFULILHDOG TTLKFVDTPE SLSGLYVFVV
481 YFNGHVEAVA YTVVSTVDHF VNAIEERGFP FTAGQPPATT KPKEITPVNF GTSPLIRYAA
541 WTGSLA
```

Figure 4

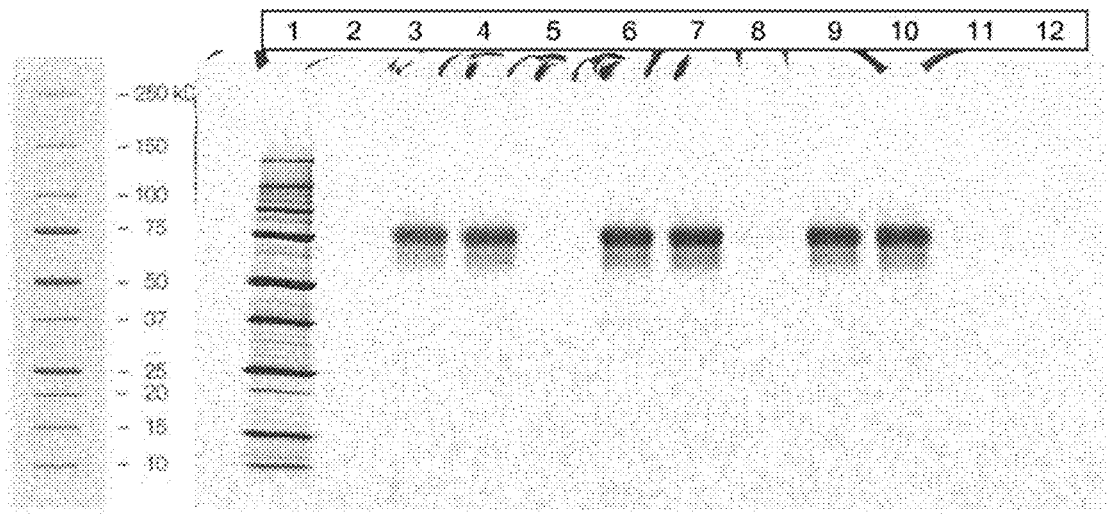
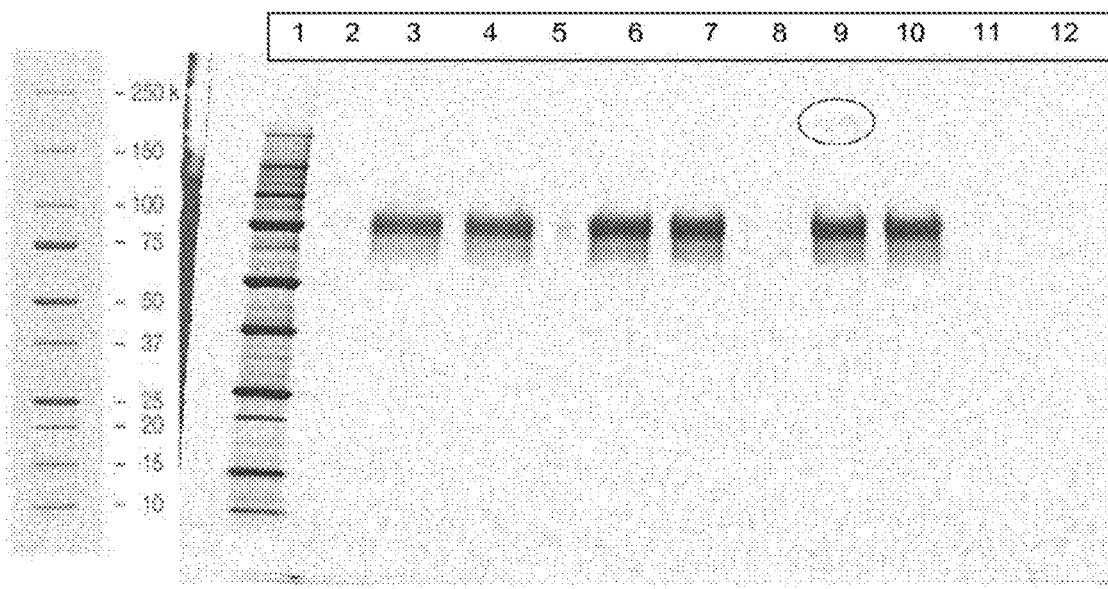
Figure 5

DRIED SAPONIN LIPOSOMAL COMPOSITION

The present invention relates to the formulation of immunogenic or vaccine compositions comprising neutral lipid liposome based adjuvants, where the composition is suitable for lyophilisation. In particular, the invention relates to lyophilised forms of such immunogenic or vaccine compositions wherein both the immunogen or vaccine antigen and the adjuvant are present in one and the same vial, as well as to the formulation and manufacture of lyophilised forms of such immunogenic or vaccine composition.

TECHNICAL BACKGROUND

Christensen et al. (2007) [Biochim. Biophys. Acta 1768 (9):2120-2129—Trehalose preserves DDA/TDB liposomes and their adjuvant effect during freeze-drying.] studied the ability of the disaccharides trehalose and sucrose to stabilise a non-phospholipid-based liposomal adjuvant composed of the cationic dimethyldioctadecylammonium (DDA) and trehalose 6,6'-dibehenate (TDB) upon freeze-drying. Trehalose in concentrations of 211 mM and above was found to protect and preserve DDA/TDB liposomes during freeze-drying, whilst sucrose had to be used in concentrations above 396 mM. The protective effect was not observed in liposomes without TDB.

Ingvarsson et al. (2013) [J. Controlled Release 167:256-264, Designing CAF-adjuvanted dry powder vaccines: Spray drying preserves the adjuvant activity] studied spray-drying of the cationic liposome adjuvant DDA/TDB using mannitol, lactose or trehalose.

Mohammed et al. (2006) [Methods 40 (1):30-8, Lyophilisation and sterilisation of liposomal vaccines to produce stable and sterile products] is also concerned with lyophilisation of cationic liposome adjuvanted vaccines. It is highlighted that in order to effectively protect liposomes from fusion the cryoprotectant should be present both internally within the liposome and in the external phase and that the intra and extra-liposomal media should have the same osmolarity. To that end, the protocol disclosed provides for the cryoprotectant to be included in the liposomes during liposome formation.

Orr et al. (2014) [J. Control Release, 177:20-6 (published electronically 2013) Elimination of the cold chain dependence of a nanoemulsion adjuvanted vaccine against tuberculosis by lyophilisation] relates to co-lyophilisation of emulsion-based adjuvant and antigen.

WO99/65465 relates to a method for agent entrapment in liposomes in the presence of a sugar.

SUMMARY OF THE INVENTION

The inventors surprisingly found that neutral lipid liposome based adjuvants can successfully be lyophilised, thus conferring thermo stabilisation of its components and allowing co-vialling of the adjuvant and antigen in dry form. The invention therefore provides compositions dried under reduced pressure from a liquid mixture comprising an adjuvant which comprises a saponin in a liposomal formulation wherein the liposomes contain a neutral lipid and a sterol, and, a cryoprotectant that is an amorphous sugar.

In addition, the invention provides methods for making such compositions. It has surprisingly been found that in order to provide for such compositions, formation of the liposomes is not required to done in the presence of the cryoprotectant.

FIGURES

FIG. 1-A illustrates with the solid line the freeze-drying cycle used for the samples of example 1; the dotted lines delineate the process acceptable range for the freeze drying of a vaccine composition comprising RTS, S antigen.

FIG. 1-B illustrates an alternative freeze-drying cycle used for the lyophilisation of vaccine compositions comprising AS01 and antigen, as exemplified in example 2; the dotted lines delineate the process acceptable range for the freeze drying of a vaccine composition.

FIG. 2-A and FIG. 2-B illustrate the preclinical immunogenicity data as obtained in example 1: FIG. 2-A. Anti-CSP cellular immune response; FIG. 2-B. Anti-CSP antibodies; I. Mosquirix™; II. Co-lyophilised RTS, S/AS01 reconstituted with 150 mM NaCl.

FIG. 4 illustrates the amino acid sequence of VZV gE as used in example 2.

FIG. 5 illustrates the SDS-page analysis of integrity of VZV gE before and after lyophilisation under different circumstances in example 2; NR refers to non-reducing conditions, R refers to reducing conditions, the legend for lanes 1 to 12 is provided in example 2.

Figure 6:
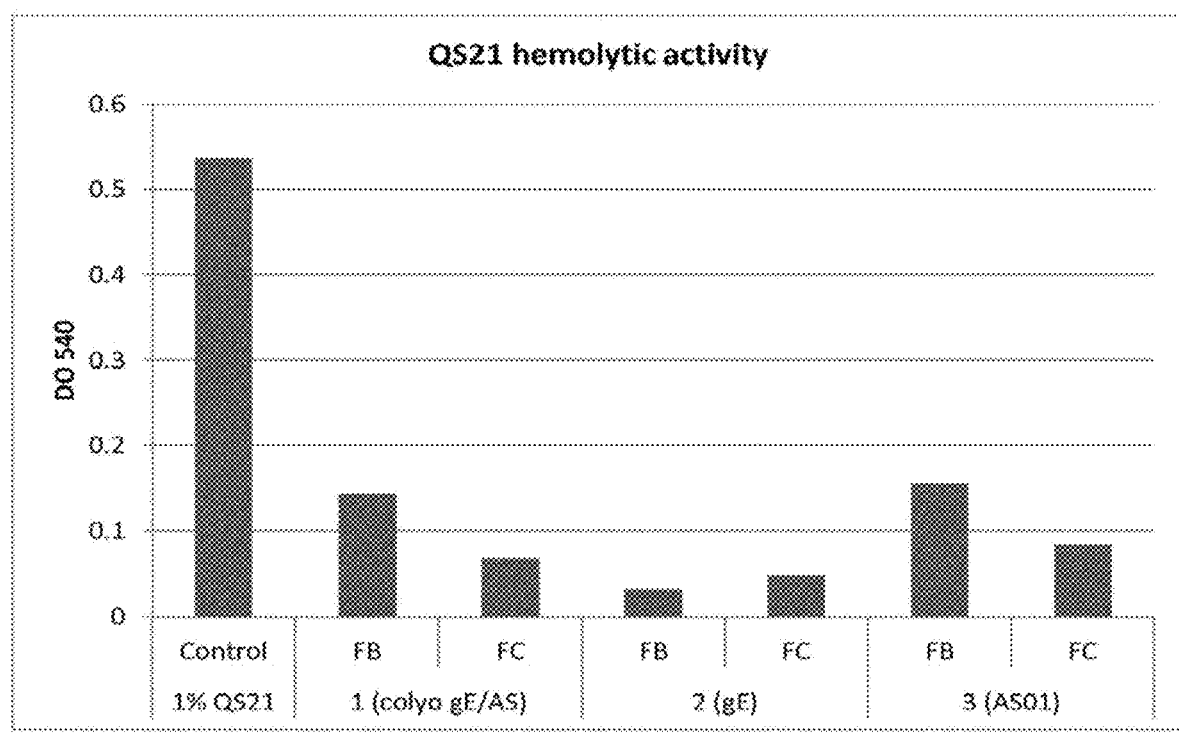

FIG. 6 shows the results of the analysis of the impact of lyophilisation on QS21 haemolytic activity in example 2; FB refers to the composition before lyophilisation, FC refers to the composition after lyophilisation.

DETAILED DESCRIPTION

While lyophilisation of vaccines containing protein, live-attenuated or inactivated virus, or bacteria—has been reported, to date, successful lyophilisation (or drying under reduced pressure in general) and thermostability characterization of neutral liposome based adjuvants has not been reported. Apart from the effect on thermostability, lyophilisation of such adjuvant could allow for co-vialing of adjuvant and antigen. Development of vaccines that reduce the need for cold-chain maintenance would reduce the cost and technological hurdles of implementation of new vaccines. Co-vialing of adjuvant and antigen might further reduce cost, logistical and technological hurdles in the distribution of vaccines worldwide.

The present invention describes the vacuum drying, such as lyophilisation, of a composition comprising neutral liposome based adjuvants, the formulation of such composition suitable for lyophilisation as well as methods for lyophilising. The inventors found that an adjuvant comprising a saponin, liposomes and optionally a lipopolysaccharide, wherein the liposomes are neutral lipid based, can be lyophilised from a mixture further comprising a cryoprotectant selected from amorphous sugars such as sucrose and trehalose. The composition may further comprise an immunogen or antigen. In particular, the inventors found that for the claimed liposomal adjuvant composition, the liposomes are not required to be formed in the presence of cryoprotectant in order for the adjuvant to retain its structural integrity and its adjuvant or immune-potentiating properties upon drying or lyophilisation. It is a further advantage of the invention that drying confers thermostability to the composition.

Following lyophilisation as described herein, the composition can be stored up to 12, to 24, or to 36 months at 30° C.; up to 6 months, or up to 12 months or 1 year at 37° C.; or, up to three months at 45° C. Suitability for storage can be based on either or both of retention of immunogenicity and retention of structural integrity of the components to an acceptable level. Structural integrity of the liposomes may be assessed by methods such as dynamic light scattering (DLS) measuring the size and polydisperity of the liposomes, or, by electron microscopy for analysis of the structure of the liposomes. In one embodiment the average particle size (by photon correlation spectroscopy) is between 95 and 120 nm, and/or, the polydispersity index (by photon correlation spectroscopy) is not more than 0.2.

From a functional perspective, antigenicity of the antigen can be measured by ELISA. Preclinical assays are available for assessing the overall immunogenicity of the compositions described herein. Immunological assays may quantify a range of responses such as CD4 T cells and/or CD8 T cells. Immunogenicity refers to the effect of the composition on the immune response upon administration of the composition to a subject.

The adjuvant in accordance with the invention comprises a saponin in a liposomal formulation and optionally a TLR-4 agonist.

Definitions

By "liposomal formulation" is meant the saponin (and optionally TLR-4 agonist) formulated with liposomes, or, stated alternatively, presented in a liposome based composition. The liposomes intended for the present invention contain a neutral lipid or consist essentially of neutral lipid, i.e. "neutral liposomes". By "neutral lipid" is understood that the overall net charge of the lipid is (approximately) zero. The lipid may therefore be non-ionic overall or may be zwitterionic. In one embodiment the liposomes comprises a zwitterionic lipid. Examples of suitable lipids are phospholipids such as phosphatidylcholine species. In one embodiment the liposomes contain phosphatidylcholine as a liposome forming lipid which is suitably non-crystalline at room temperature. Examples of such non-chrystalline phosphatidylcholine lipids include egg yolk phosphatidylcholine, dioleoyl phosphatidylcholine (DOPC) or dilauryl phosphatidylcholine (DLPC). In a particular embodiment, the liposomes of the present invention contain DOPC, or, consist essentially of DOPC. The liposomes may also contain a limited amount of a charged lipid which increases the stability of the liposome-saponin structure for liposomes composed of saturated lipids. In these cases the amount of charged lipid is suitably 1-20% w/w, preferably 5-10% w/w of the liposome composition. Suitable examples of such charged lipids include phosphatidylglycerol and phosphatidylserine. Suitably, the neutral liposomes will contain less than 5% w/w charged lipid, such as less than 3% w/w or less than 1% w/w.

The liposomes intended for the present invention further comprise a sterol. Suitable sterols include β-sitosterol, stigmasterol, ergosterol, ergocalciferol and cholesterol. In one particular embodiment, the liposomal formulation comprises cholesterol as sterol. These sterols are well known in the art, for example cholesterol is disclosed in the Merck Index, 11th Edn., page 341, as a naturally occurring sterol found in animal fat. The ratio of sterol to phospholipid is 1-50% (mol/mol), suitably 20-25%.

Where the active saponin fraction is QS21, the ratio of QS21:sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). In one embodiment, the sterol is cholesterol.

The term 'liposome' is well known in the art and defines a general category of vesicles which comprise one or more lipid bilayers surrounding an aqueous space. Liposomes thus consist of one or more lipid and/or phospholipid bilayers and can contain other molecules, such as proteins or carbohydrates, in their structure. Because both lipid and aqueous phases are present, liposomes can encapsulate or entrap water-soluble material, lipid-soluble material, and/or amphiphilic compounds.

As used herein, a 'neutral liposome based adjuvant' means the adjuvant comprises neutral liposomes for the presentation of the immune-potentiating agents included.

As used herein, 'consisting essentially of' means additional components may be present provided they do not alter the overall properties or function.

As used herein, a 'vial' refers to a container suitable for use in packaging, distributing, and using vaccines or immunogenic compositions. A vial may be 'single dose' vial (i.e., a vial containing a quantity of immunogenic or vaccine composition equal to a single dose, such as a single human dose; the specific dosage will vary depending on factors as will be apparent to one skilled in the art, such as the specific composition and the intended recipient). Alternatively, the vial may contain more than one dose ('multi-dose' vial).

As used herein, 'co-vialing' means placing at least two different components, ingredients, or compositions, in a single vial. The vial may be a single-dose vial (containing a single dose of each component, ingredient or composition), or a multi-dose vial.

As used herein, the terms 'mixture' and 'admixture' are used interchangeably.

Saponins

A suitable saponin for use in the present invention is Quil A and its derivatives. Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a preferred saponin in the context of the present invention. In a suitable form of the present invention, the saponin adjuvant within the immunogenic composition is a derivative of *saponaria* molina quil A, preferably an immunologically active fraction of Quil A, such as QS-7, QS-17, QS-18 or QS-21, suitably QS-21.

The saponin is provided in its less reactogenic composition where it is quenched with an exogenous sterol, such as cholesterol, and as provided in the liposomal formulation as defined herein above. Several particular forms of less reactogenic compositions wherein QS21 is quenched with an exogenous cholesterol exist. The saponin/sterol is presented in a liposomal formulation structure.

Methods for obtaining saponin/sterol in a liposomal formulation are described in WO 96/33739, in particular Example 1.

TLR4 Agonists

In one embodiment of the present invention, the adjuvant comprises a TLR-4 agonist. A suitable example of a TLR-4 agonist is a lipopolysaccharide, suitably a non-toxic derivative of lipid A, particularly monophosphoryl lipid A or more particularly 3-Deacylated monophosphoryl lipid A (3D-MPL).

3D-MPL is sold under the name MPL by GlaxoSmithKline Biologicals N.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-g (Th1) phenotype. 3D-MPL can be produced according to the methods described in GB 2 220 211 A. Chemically it is a mixture of 3-deacylated monophosphoryl lipid A with 4, 5 or 6 acylated chains. In the compositions of the present invention small particle 3D-MPL may be used to prepare the aqueous adjuvant composition. Small particle 3D-MPL has a particle size such that it may be sterile-filtered through a 0.22 µm filter. Such preparations are described in WO 94/21292. Preferably, powdered 3D-MPL is used to prepare the aqueous adjuvant compositions of the present invention.

Other TLR-4 ligands which can be used are alkyl Glucosaminide phosphates (AGPs) such as those described in WO98/50399 or U.S. Pat. No. 6,303,347 (processes for preparation of AGPs are also described), suitably RC527 or RC529 or pharmaceutically acceptable salts of AGPs as described in U.S. Pat. No. 6,764,840. Some AGPs are TLR-4 agonists, and some are TLR-4 antagonists. Both are thought to be useful as adjuvants.

Other suitable TLR-4 ligands are as described in WO2003/011223 and in WO 2003/099195, such as compound I, compound II and compound III described on pages 4-5 of WO2003/011223 or on pages 3-4 of WO2003/099195 and in particular those compounds described in WO2003/011223 as ER803022, ER803058, ER803732, ER804053, ER804057m ER804058, ER804059, ER804442, ER804680 and ER804764. For example, one suitable TLR-4 ligand is ER804057.

Other TLR-4 ligands which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6 (1): e16333. doi:10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7 (7): e41144. doi:10.1371/journal.pone.0041144. WO2008/153541 or WO2009/143457 are incorporated herein by reference for the purpose of defining TLR-4 ligands which may be of use in the present invention.

In a specific embodiment, the adjuvant comprises both saponin and a TLR4 agonist. In a specific example, the aqueous adjuvant composition comprises QS21 and 3D-MPL. In an alternative embodiment the aqueous adjuvant composition comprises QS21 and GLA.

A TLR-4 ligand such as a lipopolysaccharide, such as 3D-MPL, can be used at amounts between 1 and 100 µg per human dose of the adjuvant composition. 3D-MPL may be used at a level of about 50 µg, such as at least 40 µg, at least 45 µg or at least 49 µg, or, less than 100 µg, less than 80 µg, less than 60 µg or less than 51 µg. Examples of suitable ranges are between 40-60 µg, suitably between 45-55 µg or between 49 and 51 µg or 50 µg. In a further embodiment, the human dose of the adjuvant composition comprises 3D-MPL at a level of about 25 µg, such as at least 20 µg, at least 21 µg, at least 22 µg or at least 24 µg, or, less than 30 µg, less than 29 µg, less than 28 µg, less than 27 µg or less than 26 µg. Examples of lower ranges include between 20-30 µg, suitably between 21-29 µg or between 22-28 µg or between 28 and 27 µg or between 24 and 26 µg, or 25 µg.

A saponin, such as QS21, can be used at amounts between 1 and 100 µg per human dose of the adjuvant composition. QS21 may be used at a level of about 50 µg, such as at least 40 µg, at least 45 µg or at least 49 µg, or, less than 100 µg, less than 80 µg, less than 60 µg, less than 55 µg or less than 51 µg. Examples of suitable ranges are between 40-60 µg, suitably between 45-55 µg or between 49 and 51 µg or 50 µg. In a further embodiment, the human dose of the adjuvant composition comprises QS21 at a level of about 25 µg, such as at least 20 µg, at least 21 µg, at least 22 µg or at least 24 µg, or, less than 30 µg, less than 29 µg, less than 28 µg, less than 27 µg or less than 26 µg. Examples of lower ranges include between 20-30 µg, suitably between 21-29 µg or between 22-28 µg or between 28 and 27 µg or between 24 and 26 µg, or 25 µg.

When both a TLR4 agonist and a saponin are present in the adjuvant, then the weight ratio of TLR4 agonist to saponin is suitably between 1:5 to 5:1, suitably 1:1. For example, where 3D-MPL is present at an amount of 50 µg or 25 µg, then suitably QS21 may also be present at an amount of 50 µg or 25 µg per human dose of the adjuvant.

Liposomes

The liposomal formulations as intended for the present invention is defined herein above. WO2013/041572 (also published as US20140234403, incorporated herein by reference in its entirety), in particular examples 3 and 4, describes methods for making a liposome preparation of DOPC liposomes further containing cholesterol and optionally 3D-MPL, for further mixing with QS21, thereby obtaining an adjuvant in accordance with the present invention.

Antigen

The composition of the present invention may further comprise an immunogen or antigen. The antigen may be selected from bacterial, viral or cancer antigens. In one embodiment the antigen is a recombinant protein, such as a recombinant prokaryotic protein. In one embodiment, the antigen is derived from *Plasmodium falciparum*, *Mycobacterium tuberculosis* (TB), Human Immunodeficiency Virus (HIV), Moraxella, nontypable *Haemophilus influenzae* (ntHi) or Varicella Zoster Virus (VZV).

The antigen may comprise or consist of preparations derived from parasites that cause Malaria such as *Plasmodium falciparum* or *Plasmodium vivax*.

Suitable antigens derived from *Plasmodium falciparum* include circumsporozoite protein (CS protein), RTS, PfEMP-I, Pfs 16 antigen, MSP-I, MSP-3, LSA-I, LSA-3, AMA-I and TRAP. Other *P. falciparum* antigens include EBA, GLURP, RAP1, RAP2, Sequestrin, Pf332, STARP, SALSA, PfEXPI, Pfs25, Pfs28, PFS27/25, Pfs48/45, Pfs230 and their analogues in other *Plasmodium* spp.

The antigen may be an entire protein or an immunogenic fragment thereof. Alternatively the antigen may be presented as a fusion protein.

An antigen derived from *Plasmodium falciparum* CS protein may be in the form of a hybrid fusion protein. The fusion protein may contain protein derived from *P. falciparum* CS protein fused to another protein or fragment thereof. The fusion protein may contain an N-terminal or C-terminal fragment from the CS protein of *P. falciparum*. Alternatively, or in addition, the fusion protein may comprise one or more repeat units (e.g. 1, 2, 3, 4, 5, 6, 7, 8, 9 or more repeat units) from the central region of *P. falciparum* CS protein. In one embodiment, the fusion protein is a hybrid fusion protein comprising an antigen derived from CS protein together with a surface antigen from hepatitis B (HBsAg) or an immunogenic fragment thereof. Typically, the surface antigen from Hepatitis B comprises the major surface protein known as the S antigen, for example, S antigen derived from an adw serotype.

In particular, the fusion protein may comprise substantially all the C-terminal portion of the CS protein of *P. falciparum*, four or more tandem repeats of the CS protein immunodominant region, and the surface antigen from hepatitis B (HBsAg). In one aspect the fusion protein comprises a sequence of at least 160 contiguous amino acids having at least 99%, 98%, 95%, 90% sequence similarity to the C-terminal portion of the CS protein (Gaspers et al. (1989) Mol. Biochem. Parasitol 35, 185-190; Gordon et al. J Infect Dis. (1995) June; 171 (6):1576-85). In one aspect the fusion protein comprises a sequence of "substantially all" of the C terminal portion of the CS protein. As used herein, "substantially all" of the C-terminal portion of the CS protein includes the C terminus sequence devoid of the hydrophobic anchor sequence. In one aspect the fusion protein comprises a sequence consisting of the CS protein sequence devoid of the last 12 to 14 (such as 12) amino-acids from the C terminal is envisaged.

In one embodiment the fusion protein for use in the invention is a protein which comprises a contiguous amino acid sequence having at least 99%, 98%, 95%, 90% sequence similarity to amino acids 207-395 of *P. falciparum* 3D7 clone, derived from the strain NF54 (Caspers et al, supra) fused in frame via a linear linker to the N terminal of HBsAg. The linker may comprise part or all of the preS2 region from HBsAg.

A particular fusion protein for use in the invention is the fusion protein known as RTS, as described in WO 93/10152 and WO 98/05355, incorporated herein by reference in their entirety. The RTS may be in the form of RTS, S mixed particles (wherein "S" represents an unfused monomer) or as RTS. The RTS, S particles comprise two polypeptides RTS and S that may be synthesized simultaneously and which spontaneously form composite particulate structures (RTS, S) e.g. during purification. These particles may also be referred to a Virus Like Particles (VLP). Such particles can be prepared in a number of ways, for example by expressing the fusion protein in a suitable host such as yeast or bacteria.

It is believed that the presence of the surface antigen from Hepatitis B and the formation of the RTS, S particles boosts the immunogenicity of the CS protein portion of the hybrid protein, aids stability, and/or assists reproducible manufacturing of the protein.

The CS antigens may be used in conjunction with another antigen selected from any antigen which is expressed on the sporozoite or the pre-erythrocytic stage of the parasite life cycle such as the liver stage, for example liver stage antigen-1 (LSA-1), liver stage antigen-3 (LSA-3), thrombospondin related anonymous protein (TRAP), merozoite surface protein-1 (MSP1) the major merozoite surface protein, and apical merezoite antigen-1 (AMA-1). Other suitable antigens to use in conjunction with CS antigens include PfEMP-I, Pfs 16 antigen, MSP-3, LSA-3, AMA-I, TRAP, GLURP, RAPI, RAP2, Sequestrin, Pf332, STARP, SALSA, PfEXPI, Pfs25, Pfs28, PFS27/25, Pfs48/45, Pfs230.

Suitable antigens from *P. vivax* include circumsporozoite protein (CS protein) based antigens and Duffy antigen binding protein and fragments thereof, such as PvRII (see eg WO02/12292).

Suitable CS protein based antigens include a fusion protein comprising sequences derived from a CS protein of *P. vivax*. In one embodiment, the fusion protein is a hybrid fusion protein. The hybrid protein herein may contain protein derived from *P. vivax* type I and type II. In particular, the hybrid fusion protein may contain protein derived from *P. vivax* type I and type II fused to another protein or fragment thereof.

In one aspect the hybrid fusion protein comprises a hybrid protein derived from the CS proteins of *P. vivax* (CSV) and a surface antigen from Hepatitis B, such as the major surface protein known as the S antigen, such as the S antigen derived from an adw serotype.

Preferably, the fusion protein is an immunogenic hybrid fusion protein comprising: a. at least one repeat unit derived from the central repeat section of a type I circumsporozoite protein of *P. vivax*, b. at least one repeat unit derived from the central repeating section of a type II circumsporozoite protein of *P. vivax*, and c. surface antigen S derived from Hepatitis B virus.

The CSV derived antigen component of the invention may be fused to the amino terminal end of the S protein. More specifically the C-terminus end of the CSV fragment is fused to the N-terminus of said S antigen.

For example, a suitable fusion protein is CSV-S, as described in WO2008/009652.

In host cells, once expressed, the hybrid fusion protein (comprising S antigen), is able to spontaneously assemble into a lipoprotein structure/particle composed of numerous monomers of said proteins (or VLPs). Such particles can be prepared by expressing the fusion protein in a suitable host such as yeast or bacteria.

When the chosen recipient host cell strain also carries in its genome one or more integrated copies of a hepatitis B S expression cassette, the resulting strain synthesizes hybrid protein as a fusion proteins, and also non-fused S antigen. These may spontaneously be assembled into lipoprotein particles comprising monomers of the hybrid fusion protein and monomers of the S antigen. Suitable host cell for the expression of the fusion protein is for example yeast.

Also provided, is a VLP comprising CSV-S and/or RTS units. The particle may consist essentially of CSV-S and RTS units. Alternatively, the particles produced comprise or consist essentially of CSV-S, RTS and S units. Such mixed particles are described for example in WO2008/009650.

In certain embodiments the composition of the invention comprises an antigen derived from *Mycobacterium* spp., such as *Mycobacterium bovis* or *Mycobacterium tuberculosis*, in particular *Mycobacterium tuberculosis*.

Antigens of interest in the field of tuberculosis include Rv1196 and Rv0125. Rv1196 (described, for example, by the name Mtb39a in Dillon et al Infection and Immunity 1999 67 (6): 2941-2950) is highly conserved, with 100% sequence identity across H37Rv, C, Haarlem, CDC1551, 94-M4241A, 98-R6041NH-RIF-EM, KZN605, KZN1435, KZN4207, KZNR506 strains, the F11 strain having a single point mutation Q30K (most other clinical isolates have in excess of 90% identity to H37Rv). Rv0125 (described, for example, by the name Mtb32a in Skeiky et al Infection and Immunity 1999 67 (8): 3998-4007) is also highly conserved, with 100% sequence identity across many strains. Full length Rv0125 includes an N-terminal signal sequence which is cleaved to provide the mature protein.

In one embodiment the antigen is derived from Rv1196, such as comprise, such as consist of, a sequence having at least 70% identity to SEQ ID No: 1, such as at least 80%, in particular at least 90%, especially at least 95%, for example at least 98%, such as at least 99%. Typical Rv1196 related antigens will comprise (such as consist of) a derivative of SEQ ID No: 1 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv1196 are those comprising (such as consisting of) a fragment of SEQ ID No: 1 which is at least 200 amino acids in length, such as at least 250 amino acids in length, in particular at least 300 amino acids in length, especially at least 350 amino acids in length.

In one embodiment the antigen is derived from Rv0125, such as comprise, such as consist of, a sequence having at least 70% identity to SEQ ID No: 2, such as at least 80%, in particular at least 90%, especially at least 95%, for example at least 98%, such as at least 99%. Typical Rv0125 related antigens will comprise (such as consist of) a derivative of SEQ ID No: 2 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv0125 are those comprising (such as consisting of) a fragment of SEQ ID No: 2 which is at least 150 amino acids in length, such as at least 200 amino acids in length, in particular at least 250 amino acids in length, especially at least 300 amino acids in length. Particular derivatives of Rv0125 are those comprising (such as consisting of) the fragment of SEQ ID No: 2 corresponding to residues 1-195 of SEQ ID No: 2. Further immunogenic derivatives of Rv0125 are those comprising (such as consisting of) the fragment of SEQ ID No: 2 corresponding to residues 192-323 of SEQ ID No: 2. Particularly preferred Rv0125 related antigens are derivatives of SEQ ID No: 2 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 2 wherein the catalytic serine residue has been substituted (e.g. substituted with alanine). Also of interest are Rv0125 related antigens which comprise, such as consist of, a sequence having at least 70% identity to SEQ ID No: 2, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 2 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 2 corresponding to residues 192-323 of SEQ ID No: 2 wherein at least one (for example one, two or even all three) of the catalytic triad have been substituted or deleted. Particular immunogenic derivatives of Rv0125 are those comprising (such as consisting of) the fragment of SEQ ID No: 2 corresponding to residues 1-195 of SEQ ID No: 2 wherein the catalytic serine residue (position 176 of SEQ ID No: 2) has been substituted (e.g. substituted with alanine).

Suitably the antigen will comprise, such as consist of, a sequence having at least 70% identity to SEQ ID No. 3, such as at least 80%, in particular at least 90%, especially at least 95%, such as at least 98%, for example at least 99%. Typical M72 related antigens will comprise, such as consist of, a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues. Other derivatives of M72 are those comprising, such as consisting of, a fragment of SEQ ID No: 3 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from the two individual antigens Rv0125 and Rv1196, any fragment of at least 450 residues will comprise a plurality of epitopes from the full length sequence (Skeiky et al J. Immunol. 2004 172:7618-7628; Skeiky Infect. Immun. 1999 67 (8):3998-4007; Dillon Infect. Immun. 1999 67 (6):2941-2950).

M72 related antigen will comprise, such as consist of, a sequence having at least 70% identity to SEQ ID No. 3, such as at least 80%, in particular at least 90%, especially at least 95%, such as at least 98%, for example at least 99%.

Typical M72 related antigens will comprise, such as consist of, a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues.

In particular embodiments the M72 related antigen will comprise residues 2-723 of SEQ ID No. 3, for example comprise (or consist of) SEQ ID No. 3 or comprise (or consist) of SEQ ID No. 4.

A further antigen that may be employed in accordance with the present invention is the tuberculosis antigen Rv1753 and variants thereof, such as described in WO2010010180, for example a Rv1753 sequence selected from Seq ID Nos: 1 and 2-7 of WO2010010180, in particular Seq ID No: 1. Another antigen of interest in the field of tuberculosis is Rv2386 and variants thereof, such as described in WO2010010179, for example a Rv2386 sequence selected from Seq ID Nos: 1 and 2-7 of WO2010010179, in particular Seq ID No: 1. Other antigens of interest in the field of tuberculosis include Rv3616 and variants thereof, such as described in WO2011092253, for example a natural Rv3616 sequence selected from Seq ID Nos: 1 and 2-7 of WO2011092253 or a modified Rv3616 sequence such as those selected from Seq ID Nos: 161 to 169, 179 and 180 of WO2011092253, in particular Seq ID No: 167. An additional antigen of interest is HBHA, such as described in WO97044463, WO03044048 and WO2010149657.

Other antigens of interest are those comprising (or consisting of): Rv1174, also known as DPV, such as described in SEQ ID No 8 of WO2010010177; Rv1793, also known as MTI or Mtb9.9, such as described in SEQ ID No 10 of WO2010010177; Rv2087, also known as MSL or Mtb9.8, such as described in SEQ ID No 9 of WO2010010177; Rv3616, also known as HTCC1 or Mtb40, such as described in SEQ ID Nos 1 and 2-7 WO2010010177 or SEQ ID Nos 161-169, 179 or 180 of WO2011092253; and/or Rv3874, also known as CFP10 or Tb38.1, such as described in SEQ ID No 9 of WO2010010177; or an immunogenic portion (such as at least 20, 50, 75 or 100 residues therefrom) or variant thereof (such as having at least 70%, 80%, 90% or 95% identity thereto). (WO2010010177 and WO2011092253 are incorporated herein by reference in their entirety)

Tuberculosis antigens are suitably utilised in the form of a polypeptide, but may alternatively be provided in the form of a polynucleotide encoding said polypeptide.

A further antigen that may be employed in accordance with the present invention is derived from Varicella zoster virus (VZV). The VZV antigen for use in the invention may be any suitable VZV antigen or immunogenic derivative thereof, suitably being a purified VZV antigen.

In one embodiment, the VZV antigen is the VZV glycoprotein gE (also known as gp1) or immunogenic derivative hereof. The wild type or full length gE protein consists of 623 amino acids comprising a signal peptide, the main part of the protein, a hydrophobic anchor region (residues 546-558) and a C-terminal tail. In one aspect, a gE C-terminal truncate (also referred to truncated gE or gE truncate) is used whereby the truncation removes 4 to 20 percent of the total amino acid residues at the carboxy terminal end. In a further aspect, the truncated gE lacks the carboxy terminal anchor region (suitably approximately amino acids 547-623 of the wild type sequence). In a further aspect gE is a truncated gE having the sequence of SEQ ID NO. 1.

The gE antigen, anchorless derivatives thereof (which are also immunogenic derivatives) and production thereof is described in EP0405867 and references therein [see also Vafai A., Antibody binding sites on truncated forms of varicalla-zoster virus gpl(gE) glycoprotein, Vaccine 1994 12:1265-9]. EP192902 also describes gE and production thereof. Truncated gE is also described by Haumont et al. Virus Research (1996) vol 40, p 199-204, herein incorporated fully by reference. An adjuvanted VZV gE composition suitable for use in accordance of the present invention is described in WO2006/094756, i.e. a carboxyterminal truncated VZV gE in combination with adjuvant comprising QS21, 3D-MPL and liposomes further containing cholesterol. Leroux-Roels I. et al. (J. Infect. Dis. 2012, 206: 1280-1290) reported on a phase I/II clinical trial evaluating the adjuvanted VZV truncated gE subunit vaccine.

In a further embodiment, the compositions of the present invention may comprise an immunogen or antigen that is a derivative of any of the antigens described herein. As used herein the term "derivative" refers to an antigen that is modified relative to its naturally occurring form. Derivatives of the present invention are sufficiently similar to native antigens to retain antigenic properties and remain capable of raising an immune response against the native antigen. Whether or not a given derivative raises such an immune response may be measured by a suitable immunological assay such as an ELISA or flow cytometry.

Cryoprotectant

A cryoprotectant suitable for use in the present invention is an amorphous sugar such as one selected from sucrose, trehalose, lactose, raffinose, and combinations thereof. In one embodiment, the cryoprotectant is sucrose or trehalose or a combination thereof. The cryoprotectant may further comprise lyocake structure enhancing sugars such as dextran.

In an embodiment, the liquid mixture for drying, e.g. by lyophilisation, contains at least 3% (w/v), at least 4% (w/v), at least 5% (w/v), or at least 6% (w/v) of the cryoprotectant. In another embodiment the cryoprotectant is present in the liquid mixture in a total amount of less than 10%, less than 8%, less than 7%, less than 6% or less than 5.5% (w/v %). Alternatively stated, the cryoprotectant is present in the liquid mixture in a total amount of at least 4%, at least 4.5% or at least 5% (w/v %), but less than 10%, less than 8%, less than 7% or less than 6% (w/v %).

The total concentration of cryoprotectant in the liquid mixture suitably ranges from 5 to 10% (w/v) whereby at least 5% sucrose, trehalose or a combination thereof is present. In one embodiment, 5% sucrose is used. In one embodiment, 5% trehalose is used. In specific embodiments, the liquid mixture comprises at least 5% (w/v %) or between 5 and 10% (w/v %) of sucrose, trehalose or a combination thereof.

In another embodiment, the reconstituted vaccine contains at least 0.6% (w/v), at least 0.8% (w/v), at least 1% (w/v), or at least 1.2% (w/v) of the cryoprotectant. In another embodiment the cryoprotectant is present in the reconstituted vaccine in a total amount of less than 2%, less than 1.6%, less than 1.4%, less than 1.2% or less than 1.1% (w/v %). Alternatively stated, the cryoprotectant is present in the reconstituted vaccine in a total amount of at least 0.8%, at least 0.9% or at least 1% (w/v %), but less than 2%, less than 1.6%, less than 1.4% or less than 1.2% (w/v %).

The total concentration of cryoprotectant in the reconstituted vaccine suitably ranges from 1 to 2% (w/v) whereby at least 1% sucrose, trehalose or a combination thereof is present. In one embodiment, 1% sucrose is used. In one embodiment, 1% trehalose is used. In specific embodiments, the reconstituted vaccine comprises at least 1% (w/v %) or between 1 and 2.5% (w/v %) of sucrose, trehalose or a combination thereof.

In another embodiment, the ratio of cryoprotectant to liposome lipid concentration ranges from 10 to 20. In specific embodiments, the ratio is 10, 15 or 20.

In an alternative embodiment, the amorphous sugar also contributes to or provides for tonicity in the reconstituted vaccine, thus requiring a higher concentration of the amorphous sugar, such as 8 to 10% (e.g. 9.25%) sucrose (w/v) in the reconstituted vaccine, or, 8 to 10% trehalose (w/v) (e.g. 9.25%), or a combination of sucrose and trehalose in a total amount of 8 to 10% (w/v).

Further Excipients

In one embodiment, the liquid mixture is a substantially aqueous mixture optionally comprising further solvents such as ethanol or isopropanol.

In a further embodiment, a buffer is added to the composition. The pH of the liquid mixture is adjusted in view of the therapeutic components of the composition. Suitably, the pH of the liquid mixture is at least 4, at least 5, at least 5.5, at least 5.8, at least 6. Alternatively stated, the pH of the liquid mixture may be less than 9, less than 8, less than 7.5 or less than 7. In other embodiments, pH of the liquid mixture is between 4 and 9, between 5 and 8, between 5.5 and 7.5, or, between 5.8 and 6.4.

An appropriate buffer may be selected from acetate, citrate, histidine, maleate, phosphate, succinate, tartrate and TRIS. In one embodiment, the buffer is a phosphate buffer such as $Na/Na_2PO_4$, $Na/K_2PO_4$ or $K/K_2PO_4$.

The buffer can be present in the liquid mixture in an amount of at least 6 mM, at least 10 mM or at least 40 mM.

Or, the buffer can be present in the liquid mixture in an amount of less than 100 mM, less than 60 mM or less than 40 mM.

According to specific embodiments, the buffer is a phosphate buffer, present in the liquid mixture in an amount between 6 and 40 mM, such as at about 10 mM. Suitably, the buffer is selected from $Na/K_2PO_4$, $K/K_2PO_4$ and succinate. In particular, $K/K_2PO_4$ is used as buffer.

The formulation of a protein antigen for lyophilisation according to the present invention may include a surfactant. Particularly suitable surfactants for use in the present invention include polysorbates, in particular polysorbate 80 (PS80), and poloxamer 188.

In a further embodiment, the liquid mixture or dried composition contains a limited amount of NaCl, such as less than 60 mM, less than 50 mM, less than 40 mM, less than 30 mM, less than 25 mM or less than 20 mM NaCl in the liquid mixture. According to specific embodiments the liquid mixture contains less than 10% cryoprotectant, e.g. sucrose, and less than 50 mM NaCl. Alternatively, the liquid mixture contains less than 5% cryoprotectant, e.g. sucrose, and less than 30 mM NaCl.

In a further embodiment, the liquid mixture or dried composition contains a limited amount of salts, such as less than 60 mM, less than 50 mM, less than 40 mM, less than 30 mM, less than 25 mM or less than 20 mM NaCl in the liquid mixture.

Tonicity of the composition upon reconstitution can be adjusted using methods know to the skilled person such as by providing sufficient isotonifying agents in the dried composition, such as by reconstituting the dried composition with an at least isotonic solvent. In particular embodiments, tonicity of the reconstituted composition can be adjusted by adding appropriate amounts of NaCl upon reconstitution, e.g. reconstituting the dried composition with saline, or, by increasing the initial amount of cryoprotectant to levels yielding isotonicity upon reconstitution with water for injection. Alternatively the dried composition is reconstituted with an isotonic aqueous solution of a non-ionic isotonifier, e.g. sorbitol. In a preferred embodiment, the lyophilised composition is reconstituted with saline.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality in the range of 250 to 750 mOsm/kg, for example, the osmolality may be in the range of 250 to 550 mOsm/kg, such as in the range of 280 to 500 mOsm/kg.

Osmolality may be measured according to techniques known in the art, such as by the use of a commercially available osmometer, for example the Advanced® Model 2020 available from Advanced Instruments Inc. (USA).

The present invention further provides a composition as described herein for use in the treatment or prevention of disease, wherein the composition is an immunogenic composition or a vaccine composition. In a specific example of this embodiment, the invention provides an immunogenic composition such as a vaccine composition for use in the treatment or prevention of a disease associated with one or more antigen described above. In one embodiment the invention provides an immunogenic composition as described herein for use in the treatment or prevention of a disease selected from malaria, tuberculosis, COPD, HIV and herpes.

The present invention further provides methods of therapy or prophylaxis of malaria, tuberculosis, COPD, HIV or herpes in an individual in need thereof, comprising the step of providing to said individual an effective amount of an immunogenic or vaccine composition as described herein.

The invention also provides a method for producing a dried composition as described herein, comprising the steps of:
  i. Admixing a plurality of components to provide a liquid mixture, said components comprising:
     a. a liquid liposomal preparation comprising liposomes, said liposomes comprising a neutral lipid and a sterol;
     b. a saponin; and
     c. a cryoprotectant; and
  ii. drying the mixture under reduced pressure.

In one embodiment, the liquid liposomal preparation of step i(a) further comprises a lipopolysaccharide. Stated alternatively, the liquid liposomal preparation optionally comprises a lipopolysaccharide. The lipopolysaccharide is as defined herein above.

In a further embodiment, the admixed liquid composition of step (i) further (or optionally) comprises one or more components selected from antigens, immunogens, buffers, and surfactants. Thus, the method for producing a dried composition as described herein may comprise the steps of:
  i. Admixing a plurality of components to provide a liquid mixture, said components comprising:
     a. a liquid liposomal preparation comprising liposomes, said liposomes comprising a neutral lipid and a sterol;
     b. a saponin;
     c. a cryoprotectant; and
     d. one or more ingredient selected from an antigen, a buffer, and a surfactant; and
  ii. drying the mixture under reduced pressure.

As used herein, an admixed liquid composition is a composition comprising multiple components, where an isolated component need not be a liquid, but the resulting admixed composition (the mixture) is in liquid form, i.e., the admixed composition is amorphous, flows freely, and is of constant volume under a given pressure.

In one embodiment, the admixed liquid composition of step (i) comprises any two, or all three, of: an antigen, a buffer, and a surfactant. Stated alternatively, the admixed liquid composition optionally comprises any two, or all three of: an antigen, a buffer, and a surfactant.

In one embodiment of the present invention, the liposomes in the liquid liposomal preparation do not contain any cryoprotectant, e.g., were not formed in the presence of a cryoprotectant. In one embodiment of the present invention, the liquid liposomal formulation does not contain any cryoprotectant, e.g., does not contain an amorphous sugar such as one selected from sucrose, trehalose, lactose, raffinose, and combinations thereof.

In an alternative embodiment, the components of the liquid composition are admixed in a specific order. First, a solution of the cryoprotectant in water is provided, to which (if present) the buffer solution is added. Second the liquid liposomal preparation is added. Third, the saponin component is added. Fourth, (if present) the surfactant is added, and, fifth, the antigen (if present) is added. In between certain steps of the process, the mixture may be stirred for some time, e.g. 10 minutes or longer, 15 minutes or longer, 30 minutes or longer, 45 minutes or longer, or, between 15 and 45 minutes. In one embodiments the mixture is stirred after addition of the saponin. In another embodiment, the mixture is stirred for at least 15 minutes after the addition of the surfactant. In yet another embodiment, the mixture is stirred for at least 15 minutes after the addition of the antigen. In a further embodiment, the mixture is stirred for at least 15 minutes after each of the steps of adding the saponin, the surfactant and/or the antigen.

In one embodiment, some or all of the activities in step i. are performed at room temperature.

Drying under reduced pressure of a liquid mixture as provided under step ii. can be achieved using different methodologies known in the art. In one embodiment, the drying in step ii. is done by lyophilisation. The terms "freeze-drying" and "lyophilising" or "lyophilisation", and, "freeze-dried" and "lyophilised" are used interchangeably and refer to the same process of rapidly freezing a wet substance, followed by dehydration under reduced pressure. Lyophilisation or freeze-drying cycle usually consists of three process phases. In the first phase of the process, a mostly aqueous solution or mixture is frozen, i.e. "freezing of the admixed liquid composition of step i.". Subsequently, water is removed, i.e. "drying of the frozen composition", first by sublimation during primary drying. In the third phase, non-frozen water is removed by diffusion and desorption during secondary drying.

For the purpose of defining the method described the following terms are used as they are known in the art. The term "glass transition temperature" or "Tg" is the temperature at which an amorphous solid becomes soft upon heating or brittle upon cooling. The term "Tg'" refers to the glass transition temperature in the frozen state. The term "collapse temperature" or "Tc" refers to the temperature applied during the primary drying and at which an amorphous material softens to the extent that it can no longer support its own structure.

In the lyophilisation of step ii. the admixed liquid composition of step i. is frozen prior to the drying by bringing the product temperature below Tg' of the composition. In an embodiment, freezing is achieved by exposing the sample or aqueous mixture to a constant shelf temperature at a freezing temperature which is below Tg'. In an alternative embodiment, the product may be frozen by applying shelf-ramp freezing, i.e. gradually reducing the shelf temperature to a freezing temperature below Tg'. According to embodiments, the freezing temperature is a temperature below Tg' minus 5° C., below Tg' minus 7.5° C., or below Tg' minus 10° C., such as at or below −50° C.

Drying of the frozen composition under reduced pressure as contemplated in the lyophilisation of step ii. described herein will typically be done in two phases, i.e. primary drying and secondary drying. In an embodiment, drying will include:
  primary drying at a temperature below Tc of the product, and,
  secondary drying at a temperature above Tc of the product and below the Tg of the product.

In one embodiment, the drying step ii. of the method described herein is completed within 48 hours, within 36 hours, within 30 hours, within 28 hours. In a specific embodiment, step ii. is completed within 28 hours.

In one embodiment, the antigen is RTS, S and primary drying is done at a pressure lower than 90 µbar and/or above 45 µbar. Within the same embodiment, primary drying conditions may be applied for up to 19 hours and should be applied for at least 15 hours.

In an alternative embodiment, e.g. when the antigen is a VZV gE derivative, a more conservative freeze-drying cycle is used such as illustrated by FIG. 1-B.

The dried composition obtained by the method described is capable of eliciting an immune response in a subject. The said immune response is in correspondence with the adjuvant, and with any antigen present in the composition.

In one embodiment, the cryoprotectant (which may be in a liquid form or other form) is mixed with the liposomal preparation prior to mixing with the saponin. In a further embodiment, the surfactant is admixed prior to the antigen. According to another embodiment, the order of mixture is first mixing the cryoprotectant and buffer, followed by the addition of liquid liposomal preparation, saponin, surfactant, and antigen in respective order.

In the description of the method, each of the terms has the same meaning as set forth for the compositions herein.

Methods for obtaining or preparing the liposome preparation are described in WO 2013/041572, which is incorporated herein by reference in its entirety. A suitable method described therein comprises: (a) producing a lipidic film by (i) dissolving a lipid mix in isopropanol to form a homogeneous mix, and (ii) removing the solvent from the homogeneous mix to form a lipidic film, wherein the lipid mix comprises the lipid and sterol; (b) hydrating the lipidic film with a hydrating solution to form a coarse liposome suspension; (c) reducing size of the coarse liposome suspension produced in step (b) with high shear and high pressure homogenizer to form liposomes; and optionally (d) sterilising the liposomes. Suitably, step (c) comprises steps: (c') pre-homogenising the coarse liposome suspension solution with a high shear mixer, and (c") homogenising the solution produced in step (c') with a high pressure homogeniser.

Surprisingly, for the dried composition to retain its immune potentiating capacity or immunogenicity, the liposomes of the adjuvant were not required to be formed and/or formulated, e.g. during the manufacture of the liposome preparation, in the presence of a cryoprotectant.

The following examples illustrate the invention.

EXAMPLES

1. Example 1—Co-Lyophilisation of RTS, S/AS01 Vaccine (Quadridose)

RTS, S/AS01 Vaccine

The RTS, S antigen consists of two polypeptide chains, RTS and S. The RTS polypeptide contains a portion (aa 207-395) of the *P. falciparum* CS protein fused to the surface antigen (S) of the hepatitis B virus. The RTS fusion protein and the S polypeptide are coexpressed in *Saccharomyces cerevisiae* and spontaneously assemble into virus-like particles referred to as RTS, S. These purified particles constitute the RTS, S antigen as used in the formulation of the vaccine. Full details for obtaining the RTS, S antigen are available in WO93/10152, incorporated herein by reference in its entirety.

AS01 refers to a vaccine adjuvant comprising QS21, 3D-MPL in a cholesterol containing liposomal formulation.

Concentrated Liposome Bulk

The concentrated liposome bulk was prepared as described in example 3 of WO2013/041572 (incorporated herein by reference in its entirety). Briefly, the concentrated liposome bulk has been prepared in 2 steps. The first step was the lipidic film preparation. DOPC (Dioleoyl phosphatidylcholine), 3D-MPL and cholesterol were dissolved sequentially in isopropanol. Then isopropanol was stripped off under stirring and reduced pressure gradient in a warming bath at 55° C. to obtain a film residue. The pressure was then gradually reduced and a final drying was applied to obtain a lipidic film. The second step was the preparation of the concentrated liposomes bulk. To that end, the lipidic film was rehydrated in PBS to form a coarse suspension of liposomes. The liposome suspension was then homogenized with a high-shear mixer in-line with a high-pressure homogenizer to produce the desired nano-sized liposomes. The resulting concentrated liposome bulk is filtered through a 0.22 µm PES membrane. The concentrated liposome bulk for use in the example contained 40 mg/ml of DOPC, 10 mg/ml Cholesterol, 2 mg/ml MPL in 10 mM phosphate buffer (pH 6.1) and 150 mM NaCl.

Vaccine Formulation

Antigen, i.e. RTS, S, and adjuvant, i.e. AS01, were co-formulated for lyophilisation in water for injection adding
1) 30% sucrose (ad 5%),
2) 100 mM buffer, either PO4 (K/K2) or succinate, pH 6.1 (ad 10 mM),
3) 40 mg/ml liposome bulk (ad 5 mg/ml),
4) 5 mg/ml QS21 (ad 0.25 mg/ml),
followed by stirring of the thus obtained adjuvant preparation during 15 to 45 minutes at room temperature. Subsequently 3% (w/v) Polysorbate 80 (ad 0.0312%) was added and the mixture stirred during 15 to 45 minutes at room temperature. The antigen RTS, S was added ad 0.25 mg/ml and the obtained solution stirred for 15-45 minutes at room temperature. pH was measured and adjusted to 6.1 if needed.

Control formulations containing either adjuvant or antigen were also prepared. The samples tested are as follows:
1. RTS, S (lot A) PO4 (Na/Na2) pH 6.8
2. RTS, S (lot B) PO4 (Na/Na2) pH 6.8
3. AS01E3 PO4 (K/K2) pH 6.1
4. colyo RTS, S (lot A)/AS succinate 10 mM pH 6.1
5. colyo RTS, S (lot A)/AS PO4 (K/K2) 10 mM pH 6.1
6. colyo RTS, S (lot B)/AS succinate 10 mM pH 6.1
7. colyo RTS, S (lot B)/AS PO4 (K/K2) 10 mM pH 6.1
8. RTS, S (lot A) succinate pH 6.1
9. RTS, S (lot A) PO4 (K/K2) pH 6.1
10. RTS, S (lot B) succinate pH 6.1
11. RTS, S (lot B) PO4 (K/K2) pH 6.1
12. AS01 succinate pH 6.1
13. AS01 PO4 (K/K2) pH 6.1
14. Sucrose 5%

Freeze-Drying

The formulations thus obtained were filled into glass vials (0.5 ml fill volume) and lyophilized by applying a 28 hour lyophilisation cycle as presented in FIG. 1-A.

Evaluation

Several aspects were assessed to evaluate the thermal stability of the samples for up to 1 year at 4 and 30° C., 6 months at 37° C. and 3 months at 45° C.

1. Visual Aspect of the Cakes

The cakes had an elegant pharmaceutical appearance (similar to Mosquirix bidose formulation) for all formulation groups. Intriguingly, the formulations containing RTS, S but not the adjuvant displayed slight retraction. The cake appearance proved to be stable up to 12 months at 30° C. and 6 months at 37° C. A slight shrinkage was observed after 6 months at 45° C., which is probably due to a decrease in Tg because of an increased moist content of the cake.

2. Morphology of the Liposomes by Electron Microscopy

The structure of liposome was also analysed by transmission electron microscopy under a Zeiss Libra120. Negative staining analysis was performed according to standard two-step negative staining method using sodium phosphotungstate as contrasting agent (Hayat M. A. & Miller S. E., 1990, Negative Staining, Mc Graw-Hill ed.), using glow discharged carbon-formvar coated nickel grids (200 mesh) and analyzed at 100 kV. The samples were also analyzed by cryo-microscopy at 80 kV, without any contrasting agent, following vitrification at 107° K in the holes of a carbon-coated plastic mesh (Dubochet et al., 1987, in Cryotechniques in Biological EM; R. A. Steinbrecht and K. Zierold, ed; Springer Verlag). The analysis revealed that in the phosphate-buffered solutions, the liposome morphology was preserved after RTS, S/AS01 co-lyophilization and stable up to 6 months at 45° C.

3. Antigen-Adjuvant Interactions

The interaction between the RTS, S antigen and the AS01 components DOPC and Cholesterol are studied by ultracentrifugation in a sucrose gradient, followed by the quantification of RTS, S, DOPC and cholesterol in the collected fractions. The tested samples were reconstituted in 150 mM NaCl are compared to Mosquirix™ (freeze-dried RTS, S reconstituted with liquid AS01). Similar to Mosquirix™ no interaction was observed between RTS, S and the adjuvant components.

4. Liposome Particle Size

Figure 3:
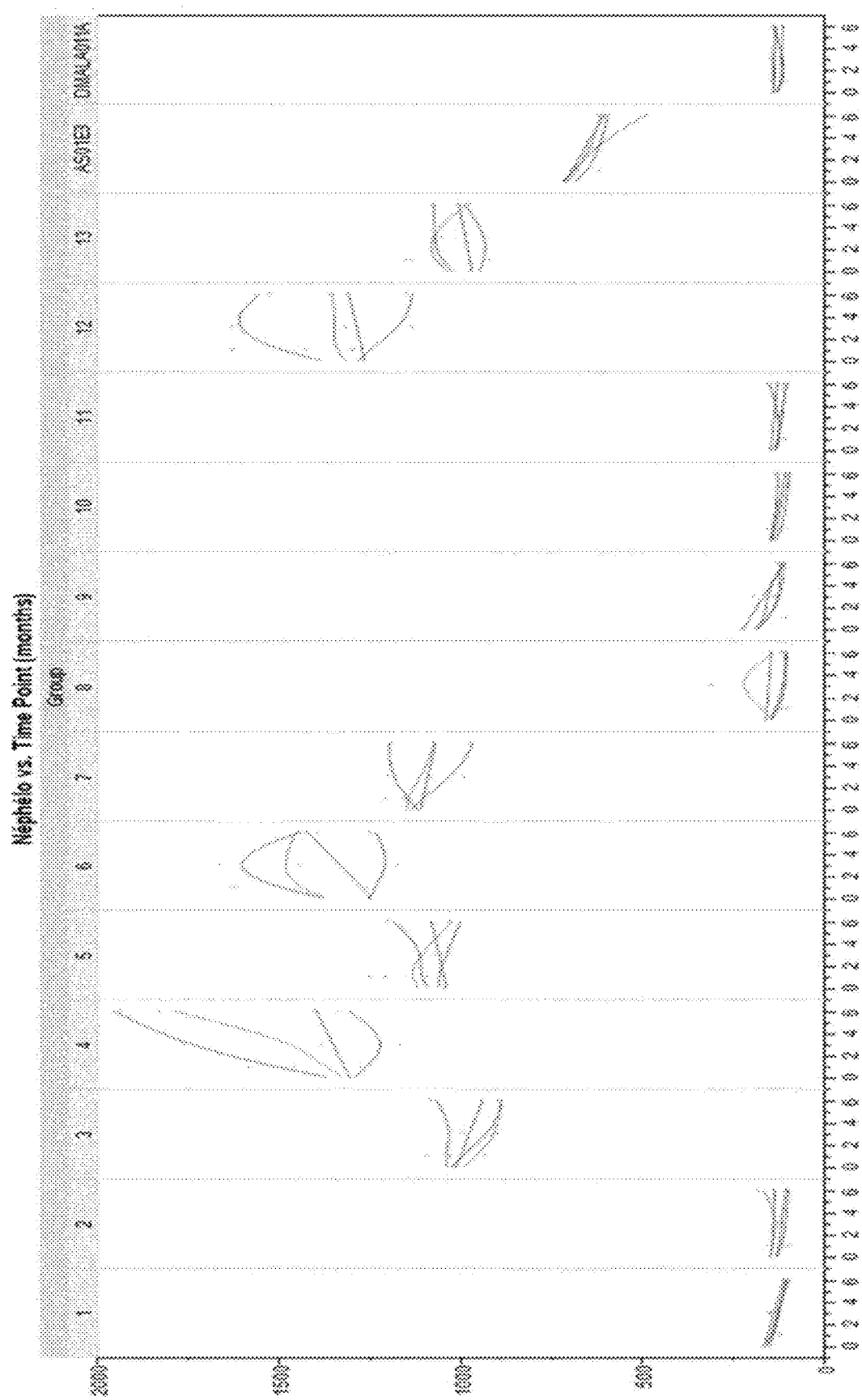
FIG. 3 illustrates the nephelometry data as obtained in example 1.

Colloidal stability was evaluated by nephelometry, indicating a lightly higher stability of phosphate-buffered formulation compared to succinate-buffered formulations. The size of AS01 liposomes in colyophilized samples was measured by DLS, indicating a hydrodynamic radius of ca 95 nm (the hydrodynamic radius in the control liquid formulation is 110 nm). This is most probably due to the presence of PS80 in the formulation (and not due to the freeze-dying step, neither to the presence of RTS, S). The AS01 liposome size remained stable over time at higher temperature. Results of the nephelometry after incubation at different temperatures are represented in FIG. 3.

5. RTS, S Particle Size

The size of RTS, S particles was measured by SEC-HPLC on a TSKgel G5000PWXL with fluorescence detection (λEx: 280 nm/λEm: 320 nm) in order to avoid interference with adjuvant components when using UV detection. The retention time of RTS, S particles in samples where the adjuvant and antigen were colyophilized was identical to the RTS, S control purified bulk and remained stable up to 1 year at 4 and 30° C., 6 months at 37° C. and 3 months at 45° C.

6. RTS and S Proteins

The integrity of RTS and S proteins was demonstrated by SDS-PAGE and ELISA. SDS-PAGE profiles were similar for up to 1 year at 4 and 30° C., 6 months at 37° C. At 45° C., some slight smears were visible after 3 months of storage. However, antigenicity by ELISA remained stable for up to 1 year at 4 and 30° C., 6 months at 37° C. and 3 months at 45° C. The antigenicity of RTS, S was measured by a mix CS-S sandwich capture ELISA (coating with monoclonal anti-CSP and revelation with a polyclonal anti-S).

7. Chemical Integrity of the Adjuvant Components

The chemical integrity of AS01 components (QS21 and MPL) was evaluated, since both components are known to be sensitive to hydrolysis. Hydrolysed QS21 (QS21H) and MPL congeners are quantified by HPLC methods. QS21 concentration and hydrolysis (QS21H) were determined by reverse phase HPLC on a Symetry RP18 column, with UV detection at 214 nm. MPL congeners were determined following derivatization with DNBA and RP-HPLC on a Waters Symmetry C18 column and fluorescence detection (excitation at 345 nm and emission at 515 nm).

QS21H remained below 3% in all freeze-dried samples. On the contrary, the QS21H content in the liquid reference adjuvant formulation (1 mg/ml DOPC, 0.25 mg/ml Cholesterol, 50 µg/ml QS21, 50 µg/ml MPL in 10 mM phosphate-buffer (pH 6.1), 150 mM NaCl) rapidly increased at high temperature (value above 3% after 1 month at 37° C. and after 3 months at 30° C.).

MPL congeners also remained stable up to 12 months at 30° C. and up to 6 months at 45° C. in all lyophilized formulations. On the contrary, the liquid reference adjuvant formulation is not stable at high temperature, as indicated by MPL deacylation (decrease of the proportion of penta and hexa congeners, together with an increase of the proportion of tetra congeners). The proportion is higher than 35% after 1 month at 45° C., after 3 months at 37° C. or after 6 months at 30° C.

8. Preclinical Immunogenicity

Immunogenicity of the co-lyophilized samples was compared to the immunogenicity of Mosquirix™ in a mouse model. The antibody responses and CD8 T-cell responses against both S and CS antigen were evaluated, as well as CD4 responses against S antigen were assessed in CB6F1 mice.

Fresh pools of leukocytes collected at different time points, were stimulated for 6 hours with pools of 15-mer peptides covering the CSP or HBs sequence. The CSP and HBs-specific cellular responses were evaluated by ICS measuring the amount of CD4+ or CD8+ T cells expressing IFN-γ and/or IL-2 and/or TNFα. All ICS analysis were performed using FlowJo software.

The study results showed that the co-lyophilization of RTS, S and AS01 had no impact on the immunogenicity (same cellular and humoral responses for both RTS and S at T0, compared to the current Mosquirix™.

Also, the co-lyophilization RTS, S/AS01 proved to be stable up to 1 year at 30° C. (and 1 year at 30° C. plus 1 month at 45° C.), 6 months at 37° C. and 3 months at 45° C. (except a slight increase of HBs-specific CD8+ T cell responses observed after 3 months at 37° C. but not at 45° C.). Upon reconstitution of lyophilized RTS, S in the liquid reference adjuvant formulation pre-incubated for 3 months at 37° C., there was a slight decrease of CSP-specific CD4+ T cell responses). The liquid reference adjuvant formulation incubated for 3 months at 45° C. could not be injected because it was proven to be haemolytic. Immune response is illustrated by FIG. 2.

2. Example 2—Colyophilisation of VZV gE/AS01 Vaccine (Unidose)

The VZV gE antigen (also referred to herein as gE) is a truncated form of the Varicella Zoster Virus glycoprotein E, has the sequence as disclosed in FIG. 4, and is obtained as disclosed in Example 2 of WO2006/094756. AS01 refers to the vaccine adjuvant comprising QS21, 3D-MPL in a cholesterol containing liposomal formulation.

The concentrated liposome bulk used is the same as described for example 1.

The antigen, i.e. VZV gE, and adjuvant, i.e. AS01, were co-formulated for lyophilisation in water for injection mixing:
1) 30% sucrose (ad 5%),
2) 100 mM buffer, either PO4 (K/K2), pH 6.1 (ad 10 mM),
3) 40 mg/ml liposome bulk (ad 2.5 mg/ml), and,
4) 5 mg/ml QS21 (ad 0.125 mg/ml), followed by stirring of the thus obtained adjuvant preparation during 15 to 45 minutes at room temperature. Subsequently 3% (w/v) Polysorbate 80 (ad 0.02%) was added and the mixture stirred during 15 to 45 minutes at room temperature. The antigen VZV gE was added ad 0.125 mg/ml and the obtained solution was stirred for 15-45 minutes at room temperature. pH was measured and adjusted to 6.1 if needed.

Control formulations containing either adjuvant or antigen were also prepared. The samples tested were as follows:
1) VZV gE/AS01
2) VZV gE
3) AS01

Freeze-Drying

The formulations thus obtained were filled into glass vials (0.5 ml fill volume) and lyophilized by applying a 40-hour lyophilisation cycle as represented in FIG. 1-B.

Evaluation

The purpose of this experiment was to evaluate the feasibility of co-lyophilisation of another antigen (VZV gE) with the adjuvant AS01. The integrity of both antigen and adjuvant were evaluated directly after co-lyophilisation.

The lyophilised material was analysed following reconstitution with 150 mM NaCl and compared to control VZV gE vaccine (lyophilized VZV gE reconstituted in liquid AS01 or in buffered saline (10 mM phosphate, 150 mM NaCl, pH 6.1).

1. Injectability

The pH measured in the different groups are slightly lower (by ca. 0.4 units) that in the control Shingrix vaccine, although the pH was fixed at 6.1 in the corresponding final bulks (before lyophilisation). The osmolality determined in the 3 groups is similar to the control.

| Group | | pH | Osmolality (mOsm/kg) |
|---|---|---|---|
| 1 (colyo gE/AS) | Before lyophilisation | 6.1 | 206 |
| | After lyophilisation | 5.8 | 436 |
| 2 (gE) | Before lyophilisation | 6.1 | 208 |
| | After lyophilisation | 5.8 | 432 |
| 3 (AS01) | Before lyophilisation | 6.1 | 209 |
| | After lyophilisation | 5.8 | 430 |
| Control | | 6.2 | 436 |

2. Morphology of the Liposomes by Electron Microscopy

The structure of liposomes was also analysed by transmission electron microscopy with negative staining, using the same protocol as in example 1.

The adjuvant displayed the characteristic morphology of the AS01 structural pattern at the EM level, i.e. liposomes of various size and shape, with membrane perforations clearly visible. The putative gE antigens were observed as very small amorphous material spread between liposomes.

The same pattern was observed in the gE/AS01 sample before and after lyophilisation, and in the to control gE cake reconstituted in AS01 adjuvant, indicating that the liposome morphology was preserved after gE/AS01 co-lyophilization.

3. Liposome Particle Size

The size of AS01 liposomes in samples was measured by DLS (in the groups containing AS01), indicating a hydrodynamic radius of ca 90 nm similar to the hydrodynamic radius in the control liquid formulation. The value obtained was close to the expected value for AS01 liposome.

| Group | | DLS_ZAD (nm) |
|---|---|---|
| VZV gE/AS01 | Before lyophilisation | 93 |
| | After lyophilisation | 91 |
| AS01 | Before lyophilisation | 91 |
| | After lyophilisation | 91 |

4. Size of gE in Solution

The size of gE antigen was measured by SEC-H PLC on a TSKgel G4000PWXL with fluorescence detection (λEx: 280 nm/λEm: 320 nm) in order to avoid interference with adjuvant components when using UV detection. The retention time of VZV gE in samples where the adjuvant and antigen were colyophilized was identical to the gE control purified bulk, indicating that the colyophilization process had no impact on the size of gE in solution.

5. Integrity of gE Protein

The integrity of VZV gE protein was demonstrated by SDS-PAGE analysis of samples before and after lyophilisation. SDS-PAGE profiles (see FIG. 5) were similar for co-lyophilized samples and VZV gE control (purified bulk and drug product), in both reducing (R) and non-reducing (NR) conditions. A slight band of higher molecular weight was observed in co-lyophilized sample, corresponding presumably to aggregation, but not representing a significant amount of protein.

| | |
|---|---|
| 1 | MW marker |
| 2 | Sample buffer |
| 3 | Control VZV gE (purified bulk) |
| 4 | Control VZV gE (reconstituted in AS01 buffer) |
| 5 | Sample buffer |
| 6 | VZV gE/AS01 before colyo (group 1) |
| 7 | VZV gE before lyo (group 2) |
| 8 | AS01 before lyo (group 3) |
| 9 | Colyo VZV gE/AS01 (group 1) |
| 10 | Lyo VZV gE (group 2) |
| 11 | Lyo AS01 (group 3) |
| 12 | Sample buffer |

6. In Vitro Potency (Antigenic Activity by ELISA)

The in vitro potency was measured by ELISA in the samples containing VZV gE. The test is an inhibition ELISA assay based on a human polyclonal antibodies directed against Varicella Zoster antigens (VARITECT®).

Briefly, serial dilutions of samples containing VZV gE antigen are incubated with a fixed amount of VARITECT®. After incubation, human anti-gE antibodies, which do not react with VZV gE antigen samples are detected by incubation on gE antigen coated microplate. The antigen-antibody complex is revealed by addition of a rabbit anti-human IgG antibody labelled with peroxidase, followed by addition of tetra methyl benzidine. The VZV gE antigenic activity is obtained by dividing the VZV gE content by the protein content (measured by Lowry). The potency, which can only be applied to final containers, is obtained by dividing the VZV gE content by the titer of the standard that was used for the validation of the method.

The ratio of in vivo potency to VZV gE content was close to 1 in all tested groups, as in the control. These results further confirmed the integrity of VZV gE antigen following lyophilisation in the presence of AS01.

| | Theoretical gE content (μg/ml) | Protein content by Lowry (μg/ml) | gE content by ELISA (μg/ml) | Antigenic activity (gE/prot) | Potency |
|---|---|---|---|---|---|
| gE/AS01 no lyo (group 1) | 125 | 128 | 123 | 0.96 | N/A |
| Colyo gE/AS01 (group 1) | 100 | 104 | 103 | 0.99 | 1.02 |
| gE no lyo (group 2) | 125 | 125 | 132 | 1.05 | N/A |
| Lyo gE (group 2) | 100 | 100 | 101 | 1.01 | 0.98 |
| Control | 100 | 94 | 108 | 1.15 | 0.92 |

7. Chemical Integrity of the Adjuvant Components

As in Example 1, the chemical integrity of AS01 components (QS21 and MPL) was evaluated in AS01-containing samples. Hydrolysed QS21 (QS21H) and MPL congeners were quantified by HPLC methods. QS21H remained below 3% in all freeze-dried samples. There was no impact of the lyophilisation process on the chemical integrity of MPL, as indicated by the similar proportions of tetra-, penta- and hexa-congeners before and after lyophilisation in both groups.

| Test | Acceptance criteria for AS01B3 | Group 1 (gE/AS01) liquid | Group 1 (gE/AS01) Colyo | Group 3 (AS01) liquid | Group 3 (AS01) Lyo |
|---|---|---|---|---|---|
| QS21H LIMIT TEST BY HPLC | Not more than 3%. | <3% | <3% | <3% | <3% |
| MPL CONGENER DISTRIBUTION BY HPLC-FLUO (Tetra-acyl component) | Between 15 and 35%. | 23.9 | 24.7 | 24.5 | 24.3 |
| MPL CONGENER DISTRIBUTION BY HPLC-FLUO (Penta-acyl component) | Between 35 and 60%. | 44.8 | 44.2 | 44.8 | 45 |
| MPL CONGENER DISTRIBUTION BY HPLC-FLUO (Hexa-acyl component) | Between 20 and 40%. | 31.3 | 31.1 | 30.7 | 30.7 |

QS21 elicits a haemolytic activity when not quenched with cholesterol within the liposomal membrane. The hemolytic activity was therefore evaluated in the AS01 containing formulations, before and after lyophilisation. Whatever the conditions tested, the hemolytic rate remained under the acceptable baseline fixed at 1% (see FIG. 6). None of them were responsible for a QS21 dequenching.

The invention claimed is:

1. A dried composition comprising an adjuvant comprising (a) a saponin in a liposomal formulation comprising liposomes containing a neutral lipid and a sterol and (b) a cryoprotectant that is an amorphous sugar, wherein the dried composition has been dried under reduced pressure from a liquid mixture comprising the adjuvant and the cryoprotectant.

2. A composition according to claim 1, wherein the drying under reduced pressure is done by lyophilisation.

3. A composition according to claim 1 wherein the liquid mixture is an aqueous mixture.

4. A composition according to claim 1 wherein the neutral lipid is egg yolk phosphatidylcholine, dioleoyl phosphatidylcholine (DOPC) or dilauryl phosphatidylcholine.

5. A composition according to claim 1 wherein the saponin is QS21.

6. A composition according to claim 1 wherein the sterol is cholesterol.

7. A composition according to claim 1 wherein the adjuvant further comprises a TLR-4 agonist.

8. A composition according to claim 7 wherein the TLR-4 agonist is a lipopolysaccharide.

9. A composition according to claim 8 wherein the lipopolysaccharide is 3D-MPL.

10. A composition according to claim 1, further comprising an antigen.

11. A composition according to claim 1 further comprising a buffer.

12. A composition according to claim 1 further comprising a surfactant.

13. A composition according to claim 1 for reconstitution/reconstituted with an isotonic solution, such as saline, prior to administration to a mammal.

14. A composition according to claim 1 for use in vaccination.

15. A composition according to claim 1 wherein the composition comprises at least 4 doses for vaccinating subjects in need thereof.

16. A method of making a composition of claim 1, comprising the steps of:
   i. admixing:
      a. the liquid liposomal preparation comprising liposomes containing the neutral lipid and the sterol, and optionally a lipo-polysaccharide;
      b. the saponin;
      c. the cryoprotectant;
      d. optionally an antigen;
      e. optionally a buffer;
      f. optionally a surfactant; and,
   ii. drying the liquid mixture provided by step (i) under reduced pressure.

17. A method according to claim 16, wherein the liquid liposomal preparation does not contain a cryoprotectant.

18. A method according to claim 16 wherein the drying under step ii is done by lyophilisation.

19. A method according to claim 18 wherein the duration of the lyophilisation cycle is less than 48 hours.

20. A method according to claim 16, wherein the order for admixing is first mixing the cryoprotectant (i.c.) and the buffer (i.e.), followed by the addition of the liquid liposomal preparation (i.a.), the saponin (i.b.), the surfactant (i.f) and the antigen (i.d.) respectively.

21. The composition according to claim 1, wherein the amorphous sugar is sucrose.

22. The composition according to claim 1, wherein the amorphous sugar is trehalose.

* * * * *